Nov. 16, 1954
C. THOMASON
PEACH TREE
Filed Dec. 31, 1953
Plant Pat. 1,321
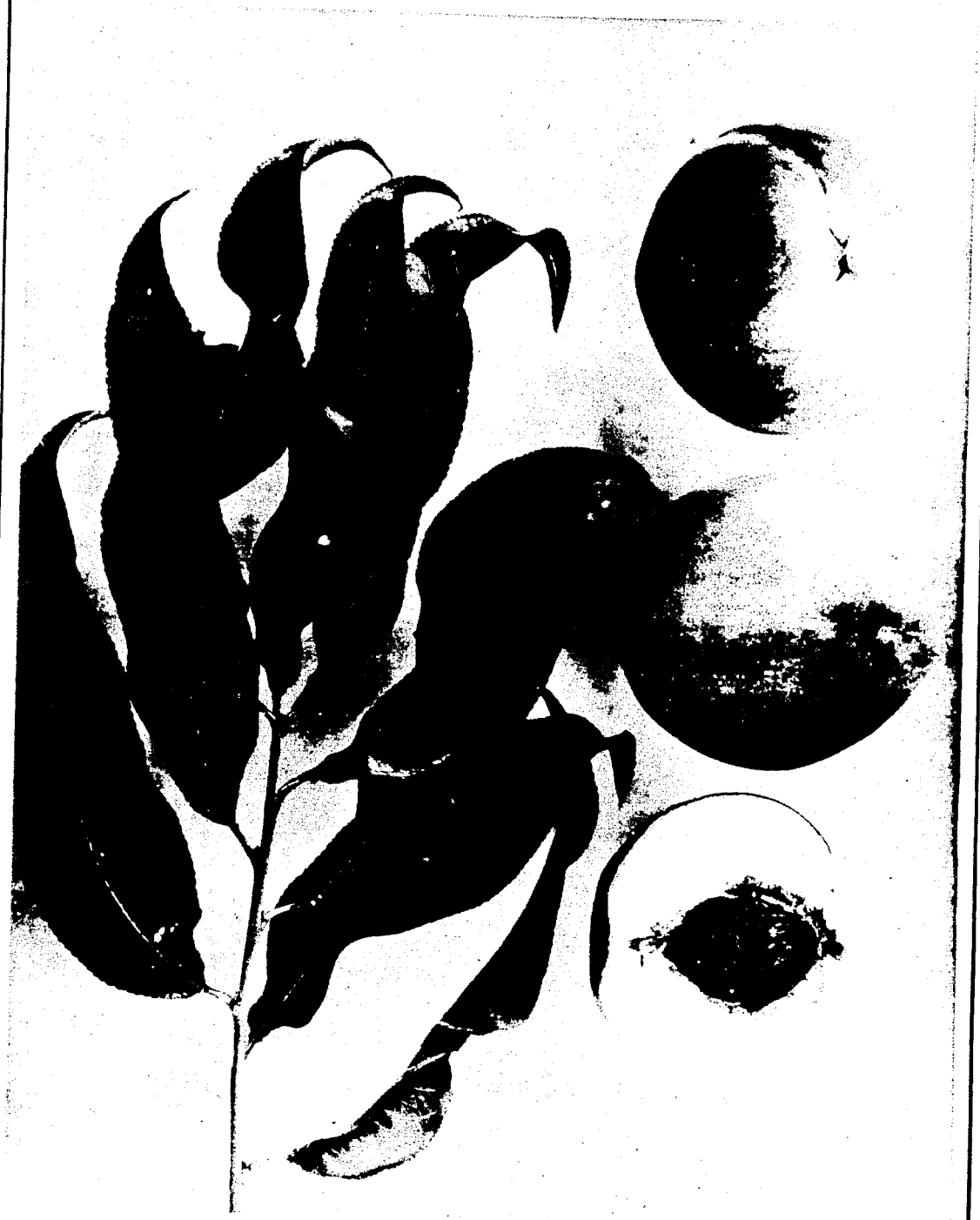
Inventor.
Charles Thomason
By: Robb & Robb
Attorneys.

United States Patent Office

Plant Pat. 1,321
Patented Nov. 16, 1954

1,321

PEACH TREE

Charles Thomason, Bangor, Ala., assignor to Stark Bro's Nurseries and Orchards Company, Louisiana, Mo., a corporation of Missouri Application December 31, 1953, Serial No. 401,744

1 Claim. (Cl. 47—62)

The present invention relates to a new and distinct variety of peach tree which was originated by me as a cross of an unnamed and unpatented seedling of "Elberta" (unpatented) × "Hal-Berta Giant" (Plant Patent No. 7).

As the result of this cross, I have produced a new variety of peach of the yellow-fleshed freestone type, the fruit of which is of exceptional high quality and has an excellent flavor, while at the same time, ripens approximately ten days later than the variety "Elberta." In addition, the fruit is characterized by its slow-softening habit after harvest, which is a distinct advantage for shipping purposes from a commercial standpoint.

The foregoing characteristics definitely distinguish my new variety from its parents, as well as from all other varieties of its class.

Asexual reproduction of my new variety by budding in test orchards near Atlas, Pike County, Illinois, shows that the foregoing characteristics and distinctions come true to form and are established and transmitted through succeeding propagations.

The accompanying drawing shows typical specimens of the foliage and fruit of my new variety, with the fruit shown in elevation, as well as in cross-section to expose the stone.

The following is a detailed description of my new variety, with color terminology in accordance with Ridgway's Color Standards and Nomenclature and with the Horticultural Color Guide, as indicated:

Observations made from specimens grown in test orchards near Atlas, Pike County, Illinois.

Dates of first and last picking—September 4th-September 9th.

Tree: Medium-large; vigorous; open; spreading; vase-formed; hardy; productive; regular bearer.

*Trunk.*—Medium stocky; smooth.

*Branches.*—Glossy. Color—Liver Brown, Plate XIV, Color No. 7′, Tone M (Ridgway). Lenticels—numerous; medium size.

*Leaves.*—Thick; smooth. Length—6½ inches. Width—1½ inches. Size — medium-large. Shape—oval; acutely pointed. Color—Spinach Green, Color No. o960, page 187, vol. 2 (Horticultural Color Guide). Margin—glandular; finely serrate. Petiole—short; thick. Glands—average number 3 to 7; alternate; large; reniform; free.

Flowers: Dates first and full blossoms—medium-late as compared with other varieties.

*Size.*—Large.

*Color.*—Azalea Pink, Color No. 618/2, page 74, vol. 1 (Horticultural Color Guide).

Fruit:

*Maturity when described.*—Eating-ripe. Date—early part of the month of September.

*Size.*—Uniform; large. Axial diameter—3¼ inches. Transverse diameter in suture plane—3⅛ inches. Diameter at right angles to suture plane—3⅛ inches.

*Form.*—Uniform; symmetrical; globose.

*Suture.*—Distinct; extends from base to apex, but discontinues at apex; has slight marked depression beyond pistil point.

*Ventral surface.*—Rounded; slightly lipped toward base; lips equal.

*Cavity.*—Flaring; elongated in suture plane, with suture showing on one side; depth ½ inch.

*Markings.*—Faint stripes.

*Base.*—Rounded.

*Apex.*—Short; rounded; pistil point apical.

*Stem.*—Stout; glabrous; medium adherence to stone.

*Skin.*—Medium-thin; tough; tenacious to flesh; no tendency to break in wet or dry seasons; has short, scant down, but does not roll up when rubbed. Color—Chrysanthemum Crimson, Color No. 824, page 169, vol. 2 (Horticultural Color Guide).

*Flesh.*—Color—Indian Yellow, Color No. 6/2, page 6, vol. 1 (Horticultural Color Guide), streaked next to stone with Delft Rose, Color No. o20, page 108, vol. 2 (Horticultural Color Guide).

*Surface of pit cavity.*—Color—Indian Yellow, Color No. 6/2, page 6, vol. 1 (Horticultural Color Guide), with fibers of Dawn Pink, Color No. 523/1, page 137, vol. 2 (Horticultural Color Guide).

*Amygdalin.*—Wanting.

*Juice.*—Moderate; rich.

*Texture.*—Firm.

*Fibers.*—Few; fine; tender.

*Ripens.*—Fairly even.

*Flavor.*—Sub-acid.

*Aroma.*—Pronounced.

*Eating quality.*—Best.

*Stone.*—Free; fibers part from flesh smoothly. Size—Medium; length 1⅞ inches; thickness ¾ inch. Form—obovoid; cuneate toward apex. Base—oblique; narrow; oval. Apex—acuminate. Sides—equal; curved on right and left sides. Surface—irregularly furrowed throughout; pitted throughout. Ridges—rounded. Pits—elongated. Ventral edge—thick; with wing throughout. Dorsal edge—narrow; with deep, narrow groove; ridges on either side interrupted.

Disease resistance: Good resistance to brown rot, as determined from comparison with other varieties grown under comparable cultural conditions in Pike County, Illinois, and at Bangor, Alabama.

Use: Market; dessert.

Keeping quality: Good.

Shipping quality: Good.

I claim:

A new and distinct variety of peach tree of the yellow-fleshed freestone class, substantially as herein shown and described, characterized particularly as to novelty by the late-ripening habit of its fruit, by the slow-softening habit of its fruit after harvest, and by the excellent flavor and high quality of its fruit.

No references cited.